United States Patent
Johnson et al.

(10) Patent No.: US 8,387,848 B2
(45) Date of Patent: Mar. 5, 2013

(54) SURGICAL STAPLE

(75) Inventors: Paul Anthony Johnson, Whitley Bay (GB); Daniel Robert Morgan Edwards, Cambs (GB)

(73) Assignee: Covidien LP, Mansfield, MA (US)

(*) Notice: Subject to any disclaimer, the term of this patent is extended or adjusted under 35 U.S.C. 154(b) by 147 days.

(21) Appl. No.: 12/819,384

(22) Filed: Jun. 21, 2010

(65) Prior Publication Data
US 2011/0042439 A1 Feb. 24, 2011

Related U.S. Application Data

(60) Provisional application No. 61/235,372, filed on Aug. 20, 2009.

(51) Int. Cl.
*A61B 17/068* (2006.01)

(52) U.S. Cl. ....... 227/175.1; 227/19; 227/902; 411/457; 411/475; 606/151; 606/219

(58) Field of Classification Search ............... 227/175.1, 227/176.1, 19, 88, 902; 411/473, 475, 457, 411/920; 606/151, 219, 324
See application file for complete search history.

(56) References Cited

U.S. PATENT DOCUMENTS

| | | | | |
|---|---|---|---|---|
| 770,479 A * | 9/1904 | Shuster | ........................... | 217/93 |
| 2,132,295 A * | 10/1938 | Hawkins | ........................ | 411/473 |
| 3,333,500 A | 8/1967 | Kelsay | | |
| 4,127,227 A * | 11/1978 | Green | ............................. | 227/83 |
| 4,691,427 A * | 9/1987 | Hill | .............................. | 29/426.5 |
| 4,887,601 A | 12/1989 | Richards | | |
| 5,366,479 A * | 11/1994 | McGarry et al. | ............. | 606/219 |
| 5,695,524 A | 12/1997 | Kelley et al. | | |
| 5,715,987 A | 2/1998 | Kelley et al. | | |
| 6,113,332 A * | 9/2000 | Hill | ............................... | 411/473 |
| 6,554,835 B1 * | 4/2003 | Lee | ................................. | 606/324 |
| 6,957,756 B2 * | 10/2005 | Lat et al. | ......................... | 227/83 |
| 7,140,527 B2 | 11/2006 | Ehrenfels | | |
| 2008/0172088 A1 | 7/2008 | Smith et al. | | |

FOREIGN PATENT DOCUMENTS

| | | |
|---|---|---|
| GB | 2069650 | 8/1981 |
| WO | 0230297 | 4/2002 |

* cited by examiner

*Primary Examiner* — Scott A. Smith
(74) *Attorney, Agent, or Firm* — Carter, DeLuca, Farrell & Schmidt, LLP

(57) ABSTRACT

A surgical staple comprising a first deformable leg, a second deformable leg and a backspan having first and second transverse portions spaced apart to create a gap therebetween. The backspan further includes a third transverse portion spaced distally from the first and second transverse portions and distally of the gap. A first non-linear backspan portion extends between the first transverse portion and the first end portion of the third transverse portion and a second non-linear backspan portion extends between the second transverse portion and the second end portion of the third transverse portion.

13 Claims, 3 Drawing Sheets

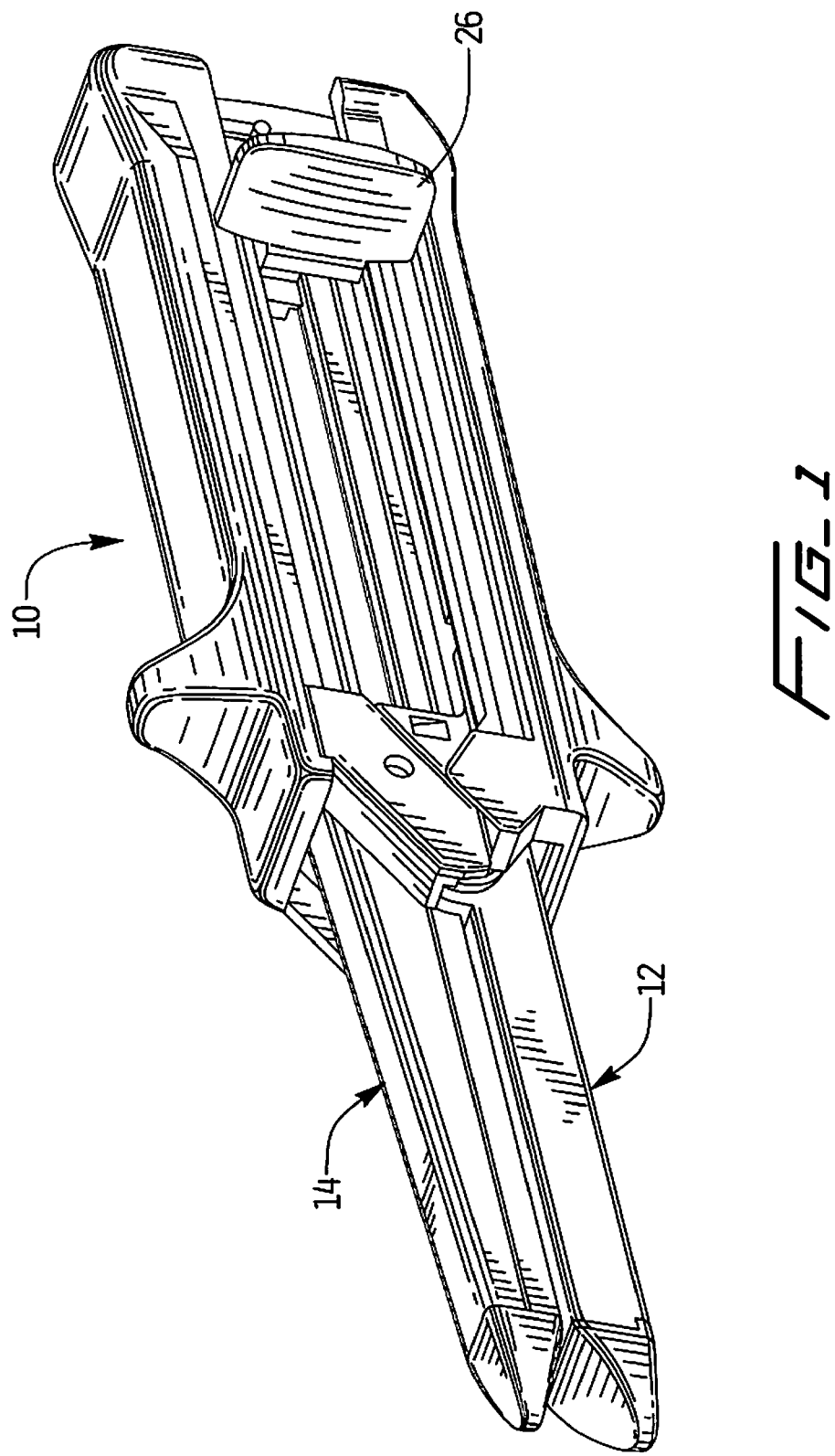

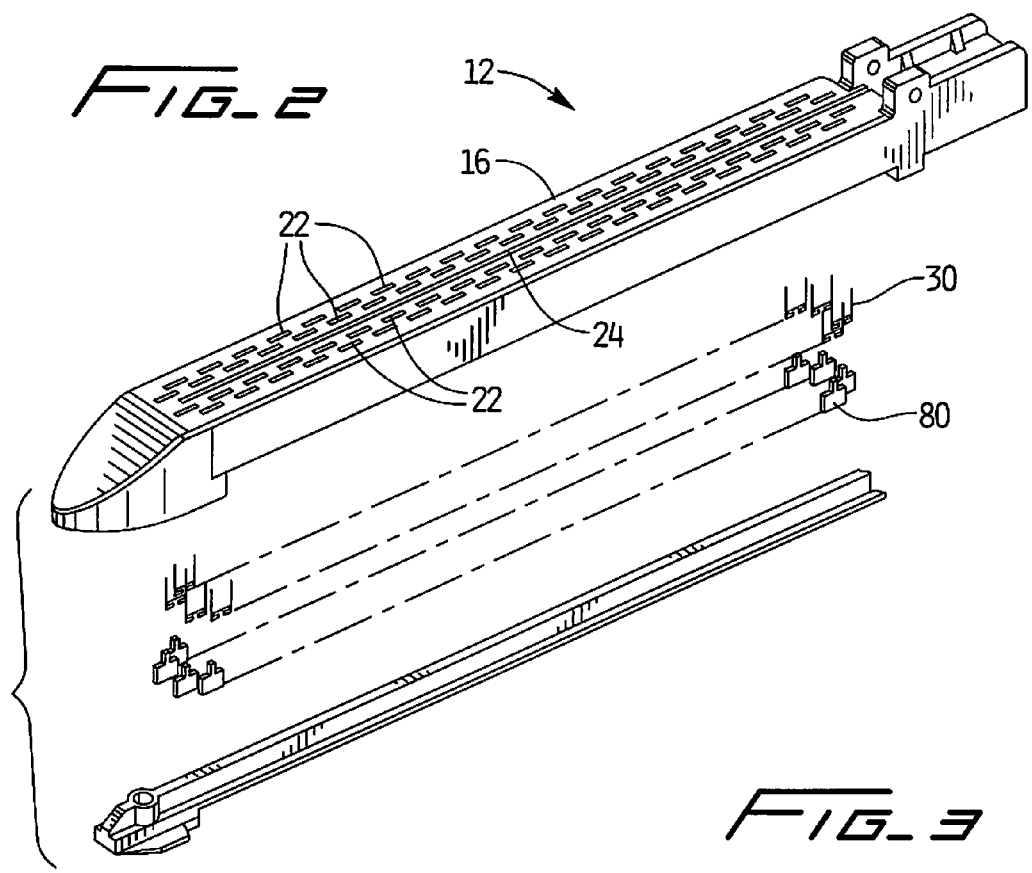
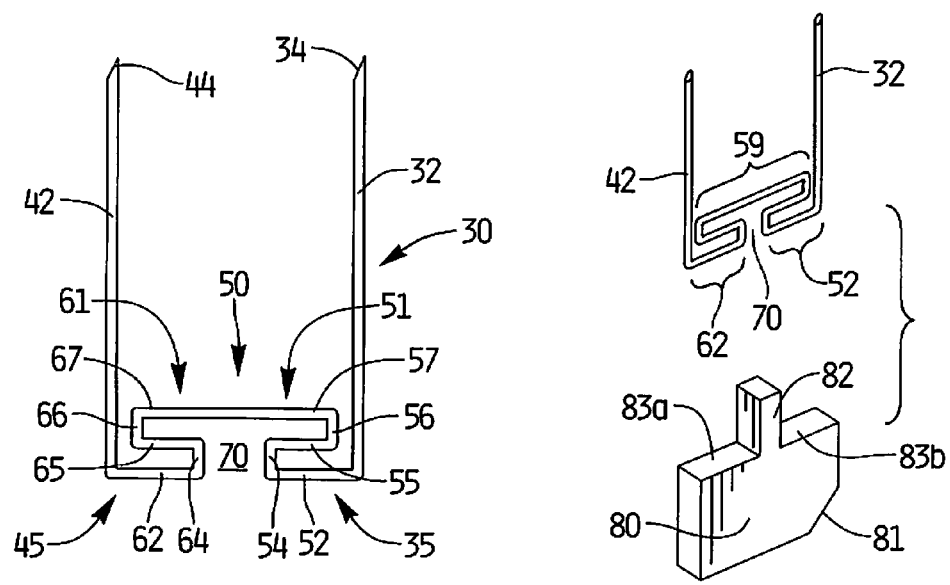

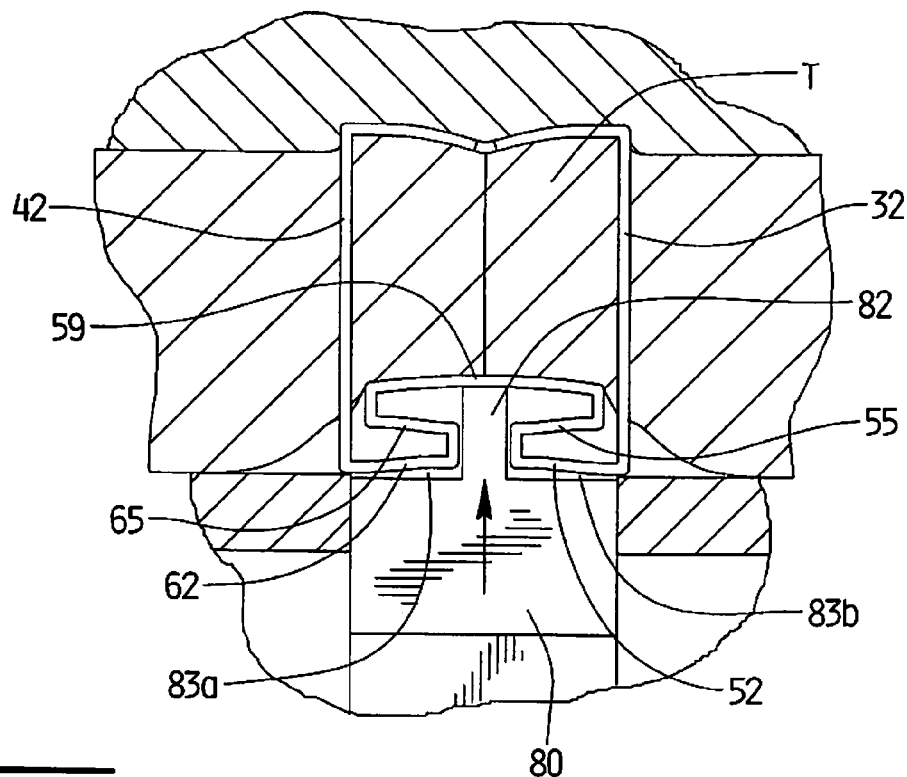
FIG_5
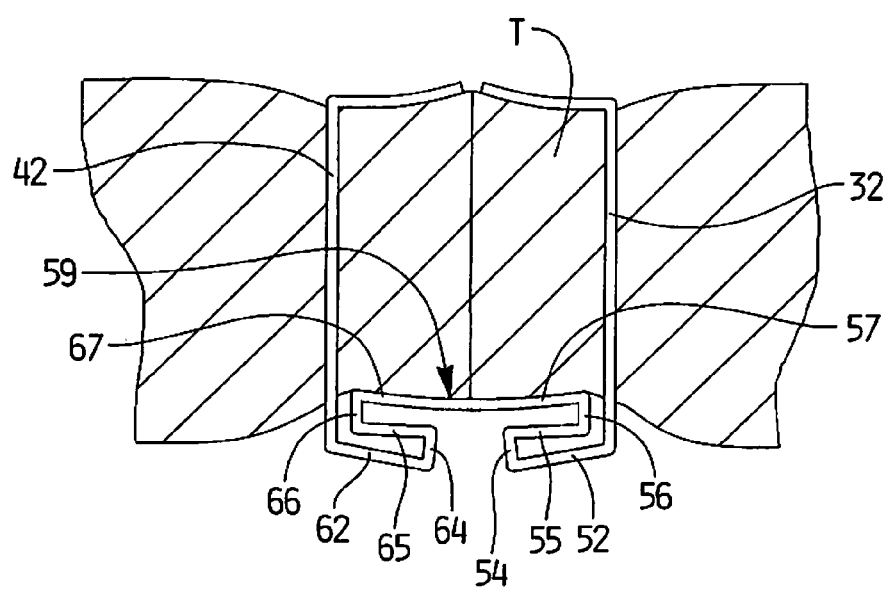
FIG_6

SURGICAL STAPLE

This application claims priority to provisional application Ser. No. 61/235,372, filed Aug. 20, 2009, the entire contents of which are incorporated herein by reference.

BACKGROUND

1. Technical Field

The present disclosure relates to a surgical staple, and more particularly, to a surgical staple configured to accommodate varying tissue compression.

2. Background of Related Art

Surgical staples are highly specialized staples that can be employed during a variety of medical procedures (e.g., surgery). Closing skin wounds, anastomosing bowels, and excising portions of a lung are just a few of the many different types of medical procedures where surgical staples can be employed.

Clinicians have turned to surgical staplers and the surgical staples associated therewith as popular alternatives to traditional suturing methods in the medical environment. Incorporating a surgical stapler into a procedure allows a clinician to quickly and easily close tissue.

Current stapling technology can employ multiple surgical staples having first and second legs, and a backspan. As is the case with most conventional surgical staples, when the surgical staple is deployed, the surgical staple penetrates tissue, creating a hole(s) and an accompanying staple line. Located along the staple line and between the legs of the surgical staple is captured tissue. The captured and now transected tissue becomes hemostatic, which results in minimal leakage of bodily fluids around the transected tissue area. However, due to stapling through variable thicknesses causing overcompression in some areas or pressure changes in the body and/or other normal body processes (e.g., healing), tissue that is not captured between the legs of the surgical staples may stretch and pull away from the legs of the surgical staples which may cause stress on the hole created by the surgical staples and/or form a path in which bodily fluids may leak, both of which, in turn, can impede the healing process.

Therefore, a surgical staple that allows for relative motion of the staple backspan after the surgical staple has been deployed into tissue may be helpful in accommodating the change in tissue, especially in the direction allowing relaxation of strain.

SUMMARY

The present disclosure advantageously provides a staple with a backspan configured and dimensioned to spring back in an amount proportional to the amount of tissue compression after staple application, thereby advantageously relaxing and reducing the risk of tissue tearing in certain procedures. Thus, the overall stiffness of the staple applied to tissue is reduced.

More specifically, in accordance with one aspect of the present disclosure, a surgical staple is provided having a first deformable leg having a first proximal portion and a first distal portion having a first tissue penetrating tip, and a second deformable leg having a second proximal portion and a second distal portion having a second tissue penetrating tip. A backspan has a first transverse portion extending from the first proximal portion of the first leg and a second transverse portion extending from the second proximal portion of the second leg. The first and second transverse portions are spaced apart to create a gap therebetween. The backspan further includes a third transverse portion having a first end portion and a second end portion, wherein the third transverse portion is spaced distally from the first and second transverse portions and distally of the gap. A first non-linear backspan portion extends between the first transverse portion and the first end portion of the third transverse portion and a second non-linear backspan portion extends between the second transverse portion and the second end portion of the third transverse portion.

In one embodiment, the first and second transverse portions lie in substantially the same plane. The third transverse portion in preferred embodiments is substantially parallel to the first and second transverse portions. In one embodiment, each of the first and second non linear backspan portions comprises a somewhat S-shaped configuration with substantially straight portions and substantially 90 degree bends.

In accordance with another aspect of the disclosure, a surgical staple is provided comprising a first deformable leg having a first proximal portion and a first distal portion having a first tissue penetrating tip, a second deformable leg having a second proximal portion and a second distal portion having a second tissue penetrating tip, and a backspan having a first region and a second region. The first region has a first transverse portion extending inwardly from a proximal portion of the first leg toward the second leg, bending distally toward the first penetrating tip of the first leg, bending back toward the first leg, bending again toward a distal portion of the first leg and bending inwardly toward the second leg. The second region of the backspan has a second transverse portion extending inwardly from a proximal portion of the second leg toward the first leg, bending distally toward the second penetrating tip of the second leg, bending back toward the second leg, bending again toward a distal portion of the second leg and bending inwardly toward the first leg.

Preferably, at least one of the bends of the first and second legs is at approximately ninety degrees. In a preferred embodiment, the first and second transverse portions of the backspan have a gap formed therebetween.

The present disclosure also provides a staple cartridge for use with a surgical stapler comprising a plurality of surgical staples supported in a spaced relation to each other wherein each of the surgical staples includes a first deformable leg, a second deformable leg, and a backspan joining the first and second legs. The backspan has a first portion extending from the first leg and a second portion extending from the second leg, wherein the first and second portions of the staple backspan are spaced apart to form a gap therebetween. A third portion of the staple backspan is positioned distal of the first and second portions. A plurality of staple pushers are movable into contact with the third portion of the staple backspan.

In preferred embodiments, the third portion of the backspan is substantially parallel to the first and second portions of the backspan.

In another aspect, the present disclosure provides a method for applying a surgical staple to tissue comprising:

providing a staple having a first deformable leg member having a first portion of a staple backspan extending therefrom and a second deformable leg member having a second portion of the staple backspan extending therefrom, the second portion of the staple backspan spaced apart from the first portion of the staple backspan to form a gap therebetween, and a third portion of the staple backspan positioned distal of the first and second portions; and advancing a pusher through the gap between the first and second portions of the staple backspan and into contact with the third portion to advance the staple legs through tissue and into contact with an anvil for deformation thereof.

In an embodiment, the step of advancing the pusher through the gap causes a projection of the pusher to contact the third portion and after a predetermined maximum movement or force of the staple is achieved during application of the staple, surface portions of the pusher contact shoulders of the staple to avoid over-straining of the first and second portions of the staple backspan.

BRIEF DESCRIPTION OF THE DRAWINGS

Various embodiments of the presently disclosed device are described herein with reference to the drawings, wherein:

FIG. 1 is a perspective view of one type of surgical instrument utilizing the surgical staples of the present disclosure;

FIG. 2 is an exploded view of the cartridge assembly of the instrument of FIG. 1 having four rows of staples;

FIG. 3 is an enlarged view of the staple and staple pusher of the present disclosure;

FIG. 4 is a side view of the surgical staple in the unformed condition; and

FIG. 5 is a side view in partial cross-section of the staple of FIG. 4 being applied to tissue; and FIG. 6 is a view similar to FIG. 5 showing the movement of the backspan in response to the force of tissue.

DETAILED DESCRIPTION

In the present disclosure, it is envisioned that the staples disclosed herein may be utilized with various stapling instruments, such as circular anastomosis staplers, linear staplers, transverse staplers, including open and laparoscopic/endoscopic staplers. FIG. 1 provides by way of example one type of surgical instrument that can be used to apply the surgical staples of the present disclosure and FIG. 2 illustrates the cartridge of the stapler 10 that contains the surgical staples. The instrument 10 is an open surgical linear stapler such as that disclosed in U.S. Pat. No. 7,140,527, the entire contents of which are incorporated herein by reference. With reference to FIG. 1, the stapler 10 has a cartridge assembly 12, an anvil assembly 14 and a slidable knob 26 to advance cam bars to contact staple pushers to advance the staples from the cartridge assembly 12 into contact with an anvil of the anvil assembly 14.

In the drawings and in the description which follows, the term "proximal", as is traditional, will refer to the end of the surgical device or instrument of the present disclosure which is closer to the operator, while the term "distal" will refer to the end of the device or instrument which is further from the operator.

Referring to FIG. 2, surgical stapling cartridge assembly 12 is illustrated having a cartridge 16 having a plurality of staple slots 22 with a knife slot 24 in between to accommodate distal movement of a knife to cut tissue between the staple rows. In the cartridge 16 shown, there are two parallel rows of staple slots 22 on each side of the knife slot 24; however, it should be appreciated that a different number of staple slots could be provided to accommodate different row configurations of staples. For example, one row of staples (and staple slots) or three rows can be provided on each side of the knife slot. The staples are designated generally by reference numeral 30 and the staple pushers are designated generally by reference numeral 80. Details of the operation of the stapler 10, e.g. clamping of the cartridge and anvil assemblies and advancement of the firing knob to fire staples, are disclosed in U.S. Pat. No. 7,140,527, incorporated by reference above.

Referring to FIGS. 3 and 4, the staple 30 will now be described. The staple is preferably composed of a stainless steel wire of circular cross-section, although other materials and wire shapes are contemplated. The staple 30 comprises in general a pair of legs 32, 42 joined by a backspan 50 having first and second spaced apart proximal transverse portions 52 and 62 and a third transverse region 59 spaced distally of the first and second transverse portions 52, 62 and accessible by a staple pusher 80 described below passing through the space (gap) 70 between the first and second transverse regions 52, 62.

More specifically, staple 30 has a first deformable leg 32 and a second deformable leg 42. The backspan 50 is divided for convenience of description into first region 51 associated with staple leg 32 and second region 61 associated with staple leg 42. Preferably, the backspan regions 51 and 61 are integral and integral with the staple legs 32, 42 so they are formed of a single wire. Each leg 32, 42 terminates in a distal tip 34, 44, respectively, configured for penetrating tissue. The proximal portion 35 of first leg 32 transitions into the first transverse backspan portion 52 of backspan 50. Similarly, the proximal portion 45 of second leg 42 transitions into the second transverse backspan portion 62 of backspan 50. First and second backspan portions 52, 62 are part of the aforementioned backspan regions 51, 61, respectively. Preferably, the staple legs 32, 42 extend substantially perpendicular to their respective backspan portion and substantially parallel to one another. However, it is also contemplated that the legs converge or diverge so that they extend from the backspan portion at a different angle than the approximate 90 degrees shown.

First transverse backspan portion 52 extends inwardly toward second leg 42, then extends distally at portion 54 toward the distal tip 34 of leg 32, then extends inwardly back toward the first leg 32 at portion 55, then extends distally at portion 56 and then inwardly toward second leg 42 at portion 57. These portions can be considered part of first backspan region 51.

The second backspan region 61 of the backspan 50 is the mirror image of the first backspan region 51. More specifically, second transverse backspan portion 62 extends inwardly toward first leg 32, then extends distally at portion 64 toward the distal tip 44 of leg 42, then extends inwardly back toward the second leg 42 at portion 65, then extends distally at portion 66, then inwardly toward first leg 32 at portion 67. These portions can be considered part of second backspan region 61.

Stated another way, the first backspan region 51 has a first transverse portion 52 connected by a somewhat S-shaped region to portion 57 of the third transverse region 59 and second backspan region 61 has a second transverse portion 62 connected by a somewhat S-shaped region to portion 67 of the third transverse region 59. Portions 57 and 67 are preferably joined so the third transverse region 59 is substantially linear and continuous as shown. First transverse portion 52 and second transverse region 62 are preferably substantially linear and spaced apart forming a gap 70 therebetween. This gap 70 allows access of the staple pusher 80 to the third transverse region 59 as described below.

The bends at the various portions of the first and second backspan regions 51, 61 are preferably about 90 degrees with substantially linear portions formed, thus having a somewhat S-shape with substantially linear portions and approximately 90 degree angles. Regions with curves and/or regions joined by different angles are also contemplated.

The pushers 80 of the cartridge assembly 12 are positioned adjacent staple slots 22 and configured to advance an individual staple 30 into engagement with the anvil of anvil assembly 14. A plurality of cam bars (not shown) are contained within the cartridge assembly 12 and are movable distally by the sliding knob 26. As the cam bars engage angled inner surface 81 of staple pusher 80, pusher 80 is advanced toward the staple slot 22 to advance the staple 30 from the cartridge 16 and into contact with an anvil wherein the staple legs 32, 42 contact and are deformed by anvil pockets to bend toward each other. The projecting finger 82 of pusher 80 passes through the gap 70 between the first and second transverse portions 52, 62 of staple 30 and into contact with the third transverse region 59, preferably in a substantially central region thereof as shown in FIG. 5. By contacting the center region rather than the shoulders, i.e., at the backspan region adjacent the transition to the staple legs, the staple 30 is placed in tissue with the backspan 50 positioned to compress the tissue and allow for subsequent flexing. That is, as the tissue expands or stretches after application of the staple 30, the backspan 50 flexes to accommodate the tissue movement This is shown for example by comparing FIGS. 5 and 6.

FIG. 5 shows application of the staple 30 by staple pusher 80. The pusher 80 is configured such that after a maximum predetermined amount of movement/force applied by finger 82 to region 59, contact of surfaces 83a, 83b of the pusher 80 with the shoulders, i.e. portions of transverse portions 52, 62 of backspan 30 adjacent legs 32, 42, takes place thus avoiding over-straining of the flexure elements during staple application.

FIG. 6 shows flexing of the backspan 50 by the tissue T as the backspan moves proximally after the staple application. More specifically, due to the bending regions of the backspan 50, the third transverse region 59 can flex toward the first and second transverse portions 52, 62, respectively, to allow for tissue expansion (push back of tissue). First and second transverse portions 52, 62 can also flex in a direction away from the formed staples leg 32, 42, providing room for tissue stretching/expansion. Thus, the compliancy/springiness of the backspan 50 of the staple 30 accommodates tissue push back on the staple, In other words, the stiffness of the staple is determined mostly by its multiple flexure spring-like backspan, rather than its legs, as the staple springs back by an amount determined by and proportional to the amount of tissue compression, thereby relaxing and reducing the risk of tearing in certain applications as it can apply a nearer to constant force/pressure on tissue.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical staple transitionable between a preformed state and a deformed state, the surgical staple comprising:
a first deformable leg having a first proximal portion and a first distal portion having a first tissue penetrating tip;
a second deformable leg having a second proximal portion and a second distal portion having a second tissue penetrating tip; and
a backspan having a first transverse portion extending from the first proximal portion of the first leg and a second transverse portion extending from the second proximal portion of the second leg, the first and second transverse portions spaced apart to create a gap therebetween, the backspan further including a third transverse portion having a first end portion and a second end portion, the third transverse portion spaced distally from the first and second transverse portions and distally of the gap, and a first non-linear backspan portion extending between the first transverse portion and the first end portion of the third transverse portion and a second non-linear backspan portion extending between the second transverse portion and the second end portion of the third transverse portion, wherein the third transverse portion in the preformed state is interposed between the first and second deformable legs.

2. The surgical staple according to claim 1, wherein the first and second transverse portions lie in substantially the same plane.

3. The surgical staple according to claim 1, wherein the third transverse portion is substantially parallel to the first transverse portion.

4. The surgical staple according to claim 1, wherein the first leg member extends substantially perpendicular to the first transverse portion and the second leg member extends substantially perpendicular to the second transverse portion.

5. The surgical staple according to claim 1, wherein each of the first and second non-linear backspan portions comprises a somewhat S-shaped configuration with substantially straight portions.

6. The surgical staple according to claim 1, wherein the non-linear backspan portions each comprise two distally extending regions joined by a transverse region.

7. The surgical staple according to claim 1, wherein the first and second legs are bent toward each other by contact with an anvil pocket.

8. The surgical staple according to claim 1, wherein the backspan is disposed entirely between the first and second deformable legs.

9. The surgical staple according to claim 1, wherein the backspan is configured to flex between the first and second deformable legs.

10. The surgical staple according to claim 1, wherein the backspan is configured to remain between the first and second deformable legs during the transition between the preformed state and the deformed state.

11. A surgical staple transitionable between a preformed state and a deformed state, the surgical staple comprising:
a first deformable leg having a first proximal portion and a first distal portion having a first tissue penetrating tip;
a second deformable leg having a second proximal portion and a second distal portion having a second tissue penetrating tip; and
a backspan having a first region and a second region, the first region having a first transverse portion extending inwardly from a proximal portion of the first leg toward the second leg, bending distally toward the first penetrating tip of the first leg, bending back toward the first leg, bending again toward a distal portion of the first leg and bending inwardly toward the second leg, the second region of the backspan having a second transverse portion extending inwardly from a proximal portion of the second leg toward the first leg, bending distally toward the second penetrating tip of the second leg, bending back toward the second leg, bending again toward a distal portion of the second leg and bending inwardly toward the first leg, wherein the backspan is configured to remain between the first and second deformable legs during the transition between the preformed state and the deformed state.

12. The surgical staple according to claim 11, wherein at least one of the bends of the first and second legs are at approximately ninety degrees.

13. The surgical staple according to claim 12, wherein the first and second transverse portions of the backspan have a gap formed therebetween.

* * * * *